United States Patent [19]

Berke

[11] Patent Number: 4,672,972
[45] Date of Patent: Jun. 16, 1987

[54] SOLID STATE NMR PROBE

[76] Inventor: Howard R. Berke, 22055 McClellen Rd., Cupertino, Calif. 95014

[21] Appl. No.: 906,631

[22] Filed: Sep. 10, 1986

Related U.S. Application Data

[63] Continuation of Ser. No. 640,670, Aug. 13, 1984, abandoned.

[51] Int. Cl.$^4$ ............................................. A61B 5/05
[52] U.S. Cl. ................................. 128/653; 324/318; 324/322
[58] Field of Search ............ 128/653, 658, 748, 303.1; 324/318, 322; 336/150, 57, 62

[56] References Cited

U.S. PATENT DOCUMENTS

| | | | |
|---|---|---|---|
| 2,719,920 | 10/1955 | Ellis | 336/150 |
| 2,961,657 | 11/1960 | Hodges et al. | 336/150 |
| 3,365,686 | 1/1968 | Petersen | 336/150 |
| 3,391,690 | 7/1968 | Armao | 128/303.1 |
| 3,448,739 | 6/1969 | Stark et al. | 128/658 |
| 3,942,519 | 3/1976 | Shock | 128/303.1 |
| 3,971,383 | 7/1976 | Van Gerven | 128/303.1 |
| 4,279,252 | 7/1981 | Martin | 128/658 |
| 4,385,636 | 5/1983 | Cosman | 128/748 |
| 4,445,892 | 5/1984 | Hussein et al. | 128/303.1 |
| 4,467,305 | 8/1984 | Ando | 336/57 |
| 4,488,135 | 12/1984 | Schwartz | 336/62 |

FOREIGN PATENT DOCUMENTS 7900245  7/1980  Netherlands ......................... 336/150

OTHER PUBLICATIONS

"A Catheter NMR Probe for In Vivo NMR Measurements of Internal Organs", H. L. Kanter, R. S. Balaban and R. W. Briggs, NIH National Heart, Lung, and Blood Institute, Bethesda, MD.
The Society of Magnetic Resonance in Medicine; Second Annual Meeting Aug. 16–19, 1983, San Francisco, California.

Primary Examiner—Kyle L. Howell
Assistant Examiner—Ruth S. Smith
Attorney, Agent, or Firm—Fitch, Even, Tabin & Flannery

[57] ABSTRACT

An in vivo NMR probe is disposed at the distal end of a catheter or endoscope for obtaining NMR spectra from within a patient. The probe is constructed from a passive integrated circuit including a receiving coil and a parametric up-converter for increasing the receivied frequency of the NMR emissions. One or more coaxial cables disposed in a lumen of the catheter connect the integrated circuit probe to an external NMR processor. The external processor may also excite the coil to radiate a localized perturbation field prior to obtaining NMR emission data of an area of interest. Alternatively, the probe may be constructed from an active circuit which enables the coil to be tuned to an NMR emission frequency of interest. A closed loop refrigeration circuit utilizing lumens in the catheter or Peltier junction devices on the integrated circuit provide for temperature stability of the active devices.

31 Claims, 5 Drawing Figures

SOLID STATE NMR PROBE

This application is a continuation of application Ser. No. 640,670 filed Aug. 13, 1984, now abandoned.

The present invention is directed to a probe for detecting NMR spectra and more particularly to such a probe which is insertable into a polarized sample to be imaged to detect NMR spectra from localized areas within said sample.

In known NMR, a sample to be magnetically imaged is placed within a relatively high magnetic field to polarize the spin axis of its molecules. The sample is then subjected to a perturbation magnetic field to upset the polarization of the spin axis. An RF receiver scans the surface of the sample to detect the electromagnetic spectra from the perturbed spin axes. Since the spin axis for various molecules will react differently, the sample can be imaged from the RF spectra emitted from the spin axes. The RF receiver includes a coil to detect the NMR spectra and to develop an electrical signal as a function thereof.

However, in many applications it is desirable to detect electromagnetic RF emissions from within the sample. However, the depth of the region imaged is approximately equal to the width of the coil of the RF receiver of the probe.

An important use for such a probe is in medical NMR imaging for diagnosis. In medical applications, a patient is inserted into an NMR scanner. The scanner is relatively large since it employs an electromagnetic coil which usually completely surrounds the patient. The prior art NMR receiver is scanned over the skin surface of the patient to obtain an NMR image.

However, in medical applications, it is highly advantageous to detect the spectra corresponding to phosphorous emissions from within the body. For example, in tumor growth, phosphorous emissions are significantly higher if the tumor is active compared to those phosphorous emissions when the tumor is malignant. However, since prior art NMR receivers cannot "see" into the body, tumors existing on organs deep within the body are not easily scanned. Also, the RF field needed to introduce a perturbation field to the magnetic polarization, must be relatively high to perturb the magnetic spin axis of the phosphorous molecules within the body of the patient.

A prior art probe for in vivo measurement is known for measurement of NMR spectra from within a canine heart. The probe is disposed at the end of a catheter and includes a two turn solenoid which is passed through a superficial cutdown in an external jugular vein. The coil is positioned in the apex of the right ventricle by fluoroscopic monitoring. NMR spectra are collected by usual means. A disadvantage and limitation of such an in vivo probe is that because of the size of the solenoid, the probe must be surgically implanted by passing the catheter through the surgical incision. Another disadvantage and limitation of the prior art in vivo probe is that the solenoid is subject to body temperature and is not easily cooled. Cooling of the solenoid below body temperature is desirable to minimize thermo-resistive variations in the impedance of the solenoid.

Another application for a probe which can "see" within a sample is on quality assurance automated equipment for the chemical and pharmaceutical industries. An automated processing line could pass magnetically polarized samples of a chemical solution under the probe. The probe can then be inserted into the solution for detecting the electromagnetic spectra of the polarized spin axis. Thus, the molecular composition of the solution could then be determined and a decision made on whether said solution is within quality control specifications.

SUMMARY OF THE INVENTION

It is therefore an object of the present invention to overcome one or more of the disadvantages and limitations enumerated above.

It is a primary object of the present invention to provide an NMR probe which is intrusively insertable into a sample for obtaining local NMR spectra.

It is an important object of the present invention to provide a probe at a distal end of the catheter which does not require a surgical incision to pass the NMR probe therethrough.

It is a further object of the present invention which minimizes the size of the probe by integrated circuit techniques.

Yet another object of the present invention is to provide cooling of the probe to eliminate thermoresistive disturbances of the RF coil when inserted in a body.

Yet another object of the present invention is to provide an NMR probe which relies on passive circuit elements for temperature stability.

According to the present invention, an NMR probe for detecting NMR spectra emitted from within a sample includes an integrated circuit carried at a distal end of the probe. The integrated circuit includes a coil for converting the detected NMR spectra into an electrical signal. The size of the coil is selected in accordance with the frequency of the spectra desired to be scanned. The integrated circuit also includes a parametric up-converter or other means for converting a first electrical signal with a first frequency into a second electrical signal with a second frequency greater than said first frequency the electrical signal developed by the coil. By increasing the frequency of the signal, the effective temperature of the coil is lowered thereby minimizing the requirement for cooling of the coil. However, in one aspect of the present invention, additional cooling of the coil may be provided by conventional refrigeration means or by integrated Peltier junction devices.

The probe also includes means for conducting the converted signal to an external processing means of a typical NMR system. The external processor includes means for impedance matching the coil to the impedance of the sample to maximize power transfer.

In one aspect of the present invention, the parametric converter includes a passive parametric amplifier which has an integrated circuit capacitor. The capacitor sinusoidally varies at a selected second frequency higher than the detected first frequency. The converted signal has a frequency which is the sum of the first and second frequencies. The integrated capacitor may be formed from the reverse bias PN junction of an integrated circuit diode. The processor means would include means for developing a further electrical signal for reverse biasing the diode and modulating the depletion region width of the reverse bias PN junction. The conducting means conducts the further electrical signal to the diode.

In another aspect of the present invention, where localized spectra are desired to be imaged, such as phosphorous emissions, the integrated circuit coil may also be operated as a transmitter of the perturbation electromagnetic field. The conducting means may conduct a signal from the external processor to the coil for developing the excitation perturbation field.

These and other objects, advantages and features of the present invention will become more apparent from the following description when read in conjunction with the accompanying drawings and the appended claims.

DESCRIPTION OF THE PREFERRED EMBODIMENT

Figure 1:
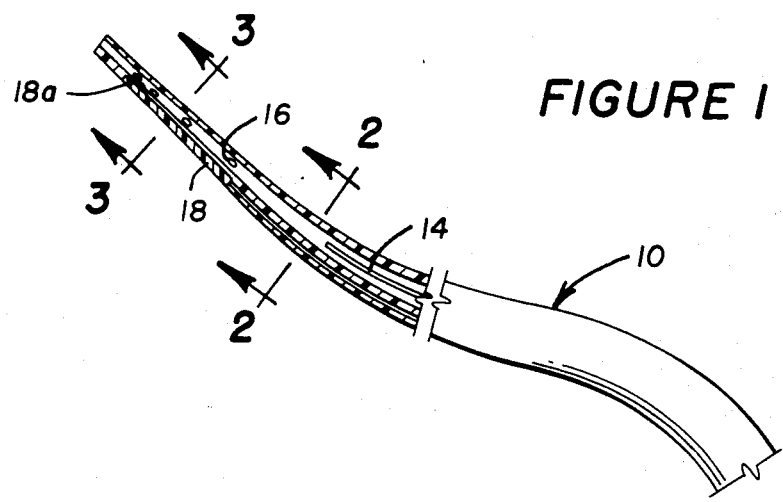
FIG. 1 is a diagrammatic illustration, partially in cross section of a typical catheter useful in practicing the present invention.
Figure 2:
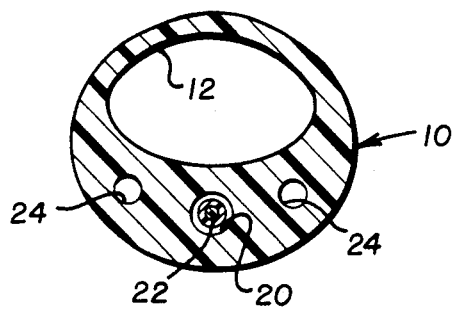
FIG. 2 is a cross sectional view of the catheter taken along line 2—2 of FIG. 1.
Figure 3:
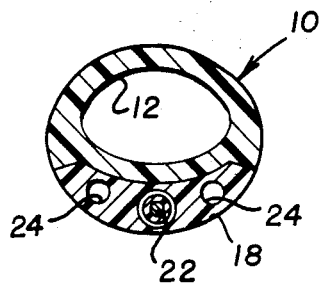
FIG. 3 is a cross sectional view of the catheter taken along line 3—3 of FIG. 1.

Referring now to FIGS. 1-3, there is shown a catheter/endoscope 10. Catheter/endoscope 10 includes a lumen 12 for obtaining a biological fluid sample or making an infusion into an artery. For example, an angiographic catheter will obtain a sample of blood within lumen 12. The diameter of catheter/endoscope 10 ranges typically from a minimum of 2 millimeters for an angiographic catheter to a centimeter or more for an endoscope insertable through external body orifices. A typical angiographic catheter also includes a guide wire 14, shown partially in FIG. 1, which is received by lumen 12 and normally extends out the tip of the angiographic catheter to provide a guide or track for catheter 10 when it is necessary to guide catheter 10 through relatively sharp ends, for example, in an artery. Catheter 10 may also include a plurality of side holes 16 at its distal end for facilitating the receiving of a fluid sample.

Catheter/endoscope 10 has an outside diameter adequate to allow for the non-traumatic, minimally invasive, percutaneous or intraorificial introduction and passage of the device. Materials selected for the construction of catheter/endoscope 10 are non-thrombogenic and non-toxic substances that also selected for the magnetic susceptability so that catheter/endoscope 10 may be rapidly visualized during scanning of the NMR spectra.

An NMR probe 182 is embedded within a probe head region 18 disposed at the distal end of catheter/endoscope 10. Probe head region 18 is preferably fabricated from the same material as catheter/endoscope 10. Catheter/endoscope 10 includes at least one further lumen 20 through which one or more coaxial conductors 22 are disposed. Coaxial conductors 22 provide means for conducting electrical signals from the probe head, hereinbelow described, to an external processor, of the NMR scanner (not shown). Coaxial conductor 22 to meet the requirements of the relatively small size of lumen 22 is fabricated from an extruded gold filament which is insulated with an appropriate dielectric with a shielded metallization surrounding the dielectric. Coaxial conductors of the requisite size for practicing the present invention are commercially available. Catheter/endoscope 10 may also include further lumens 24 for carrying additional coaxial cables, similar to coaxial cable 22, or be used for conducting additional fluids, as hereinbelow described.

Figure 4:
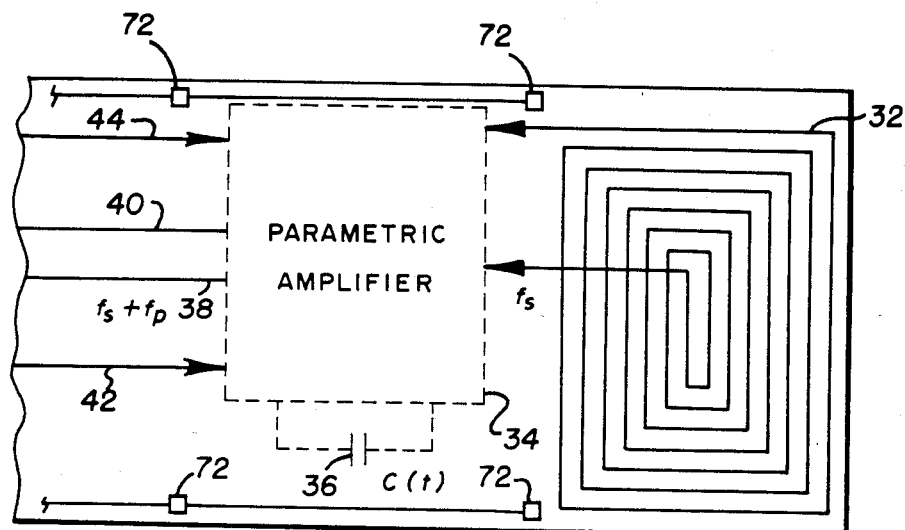
FIG. 4 is a schematic diagram of an integrated circuit probe for use with the catheter shown in FIG. 1.

Referring now to FIG. 4, there is schematically shown one embodiment of an integrated circuit NMR probe 30 of the present invention. Integrated circuit 30 includes an integrated circuit coil 32 for converting the detected NMR spectra into an electrical signal having a frequency $F_s$. Coil 32 is coupled to a parametric amplifier 34 for frequency up-converting the electrical signal applied thereto. Parametric amplifier 34 includes a capacitor 36 having a time variable capacitance. When the capacitance of capacitor 36 sinusoidally varies at a second selected frequency $F_p$, parametric amplifier 34 develops an output signal along the line 38 having the frequency of the algebraic sum of $F_s$ and $F_p$. Line 38 is conventionally bonded to a center conductor of coaxial cable 22 by conventional bonding means as is known in the art of fabricating integrated circuits. A line 40 is bonded to the shielding conductor of coaxial cable 22. A line 42 is bonded to the center conductor of a further coaxial cable (not shown) which provides a signal for sinusoidally varying the capacitance of capacitor 36.

In one embodiment of the present invention, capacitor 36 is an integrated circuit diode operated in a reverse bias condition. The signal applied to line 42 has a DC component for reverse biasing the integrated circuit diode and an AC component for modulating the depletion region width of the reverse bias PN junction. By modulating the depletion region width, the inherent capacitance of a reverse bias PN junction is sinusoidally varied.

Coil 32, and lines 38, 40 and 42 are formed from depositing a metallization layer on oxide grown on integrated circuit 30 and selectively etching to form a continuous conductive path. Note that coil 32 requires a further oxidation and second metallization to provide a conductive path from the center of the coil to parameteric amplifier 34 when coil 32 contains more than one loop. The number of loops of coil 32 is determined by the frequency of the NMR spectra desired to be measured. The width of coil 32 is approximately equal to the depth of the sample from which the NMR spectra are to be determined.

In some applications, it is desirable to also operate coil 32 as a transmitting antenna for a perturbation field. A further conductor 44 may also be disposed on integrated circuit 30 and operatively coupled through parametric amplifier to coil 32. A further coaxial cable, similar to cable 22, may provide an RF signal developed by the external processing means of the NMR scanner to apply an RF signal to coil 32. In response to such RF signal, coil 32 radiates an electromagnetic field to provide a localized perturbation to the resonance spin axis of the desired spectra.

Parametric amplifier 34 is well known in the art. Known semiconductor parametric amplifiers are described in Semiconductor-Diode Parametric Amplifiers, Blackwell and Kotzebue, Prentiss Hall, 1961. Another function of parametric amplifier 34 is to provide impedance matching between the impedance of coil 32 and the impedance of coaxial conductor 22 to maximize power transmissions of the signal. Also, by increasing the frequency of the electrical signal at frequency $F_s$ the effective temperature of coil 32 as seen by external processing means is lowered by a factor commensurate with frequency $F_p$. Thus, coil 32 need not be additionally cooled when inserted into a body to reduce thermal noise of thermal resistive changes of coil 32. However, additional cooling means may be provided with integrated circuit 30 as hereinbelow described.

Figure 5:
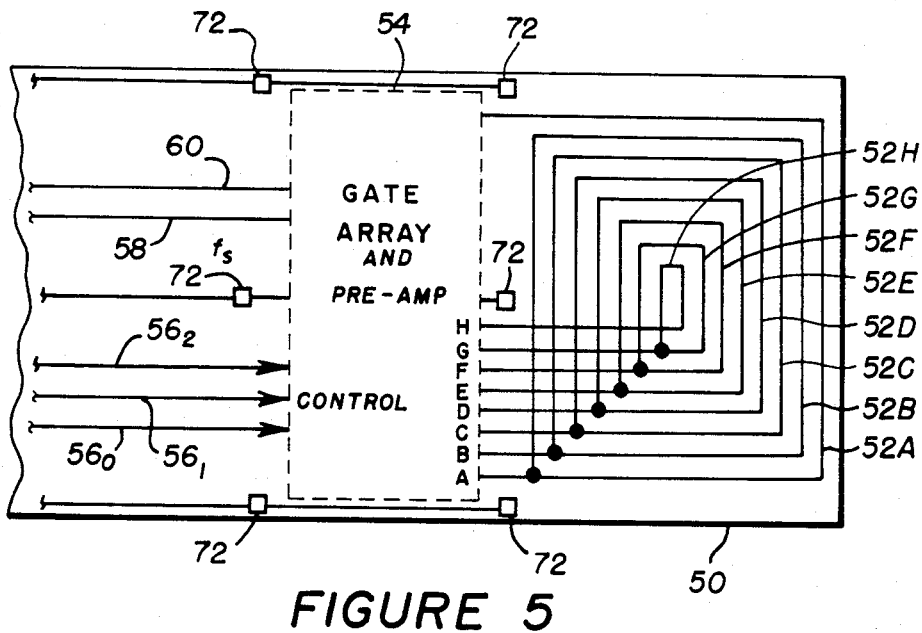
FIG. 5 is an alternate embodiment of the integrated circuit probe according to the present invention.

Referring now to FIG. 5, there is shown an integrated circuit 50, incorporable in probe 10 of FIG. 1 and including active components. An active gate array 54 is programmed to select one of coils 52A-H. For example, if coil 52A is selected, a one-turn coil is provided. Similarly, if coil 52H is selected an 8-turn coil is selected. The number of turns of the coil selected may thus be programmed remotely from the external processor. An appropriate binary control signal is developed by the external processor and applied to appropriate coaxial conductors through catheter/endoscope 10 to control lines $56_{0-2}$. Control lines $56_{0-2}$ are conventional metallization paths on integrated circuit 50. Gate array 54 may include common base bipolar transistors to selectively couple one of outputs A-H to an output line 58 which carries the electrical signal developed by coil 52 in response to the NMR spectra and having a frequency $F_s$. A further lead 60 is bonded to the external conductor of coaxial cable 22 as hereinabove described. Gate array 54 may also include preamplifier means and filter means for filtering the electrical signal at frequency $F_s$.

When the NMR probe is constructed in the form of an integrated circuit 50, the active components thereon need to be cooled to obtain temperature stability. When such active components will be subjected to the internal body temperature of a patient. Otherwise, without cooling, thermal noise may obscure the detected NMR spectra. Accordingly, lumens 24 carry a cooling fluid to probe tip region 18 for maintaining a constant temperature below body temperature thereof. For example, cooling means may include a well known closed loop refrigeration circuit. The external cooling system components 70, e.g., the condenser, compressor and expansion valve of such a cooling circuit, are disposed external of catheter/endoscope 10. Lumens 24 provide means for conducting the cooling fluid and also provide the evaporator function of a closed loop cooling system.

In another embodiment of the present invention, cooling means may be integrated on integrated circuit 30 or 50 in the form of Peltier junction devices 72. Such Peltier junction devices comprise reverse bias diodes which have thermal characteristics across the PN junction similar to that of dissimilarities across metallic thermocouples. By regulating the reverse bias voltage across the Peltier junction, temperature stability of the active component of gate array 54 and of coil 52 may be maintained.

Of course, the present invention need not be restricted to medical applications as hereinabove described. The apparatus of the present invention is useful whenever an integrated circuit NMR probe has utility for obtaining NMR spectra within a sample. It should therefore be obvious that numerous uses and modifications to the present invention can be made by those skilled in the art without departing from the inventive concepts disclosed herein which are defined by the scope of the appended claims.

What is claimed is:

1. An NMR probe for providing to a processing means an electrical representation of NMR spectra emitted from and within a sample, said probe comprising:
   a probe body with a distal end;
   an integrated circuit carried at said distal end of said probe body for insertion into a sample, said integrated circuit including coil means for converting electromagnetic energy representing an NMR spectrum into a first electrical signal having a selected first frequency and converter means for converting said first electrical signal into a second electrical signal with a second frequency greater than said first frequency; and
   means for conducting said second electrical signal to a processing means.

2. An NMR probe as set forth in claim 1 wherein said probe body comprises NMR visible material.

3. An NMR probe as set forth in claim 1 wherein said coil means includes metalization disposed on a surface of said integrated circuit.

4. An NMR probe as set forth in claim 1 wherein said probe further includes:
   means for cooling said integrated circuit to a substantially constant temperature below the temperature of said sample.

5. An NMR probe as set forth in claim 4 wherein said cooling means includes a plurality of Peltier junction devices integrated into said integrated circuit, and wherein said conducting means includes means for receiving an electrical driving signal for driving said Peltier junction devices, said conducting means also including means for conducting said driving signal to said Peltier junction devices.

6. An NMR probe as set forth in claim 5 wherein said Peltier junction devices are disposed proximate to said coil for reducing thermo-resistive variation in the impedance said coil.

7. An NMR probe as set forth in claim 1 wherein said conducting means includes means for receiving an electrical perturbation signal at a selected perturbation frequency and for conducting said perturbation signal to said coil so that said coil can radiate an electromagnetic field in response to said perturbation signal for selectively modulating the magnetic polarization of a sample proximate to said integrated circuit.

8. An NMR probe for providing to a processing means an electrical representation of NMR spectra emitted from and within a sample, said processing means including a means for generating a control signal at a selected frequency said probe comprising:
   a probe body with a distal end;
   an integrated circuit carried at said distal end of said probe body for insertion into a sample, said integrated circuit including coil means for converting electromagnetic energy representing an NMR spectrum into a first electrical signal having a selected first frequency and converter means for converting said first electrical signal into a second electrical signal with a second frequency greater than said first frequency; and
   means for conducting said second electrical signal to the processing means;
   said converter means comprising:
   a passive parametric amplifier having an integrated circuit capacitor, said capacitor having a capacitance which can be sinusoidally varied in response to said control signal, said second frequency being the sum of said first and selected frequencies; and
   means for coupling said control signal to said parametric amplifier.

9. An NMR probe as set forth in claim 8 further comprising means for generating and coupling a reverse biasing potential to said integrated circuit capacitor, wherein said capacitor includes:

an integrated circuit diode having a p-n junction coupled to said means for coupling a reverse biasing potential, the depletion region width of said reverse biased p-n junction varying in response to said control signal.

10. An NMR probe as set forth in claim 9 wherein said conducting means includes one or more coaxial cables disposed within said probe.

11. An NMR probe for converting an NMR spectrum into an electrical signal analyzable by a processing means, said probe comprising:
a probe body having a distal end;
a plurality of lumens disposed longitudinally within said probe body;
an integrated circuit carried at said distal end of said probe body, said integrated circuit including first converter means for converting detected NMR emissions into a first electrical signal having a first frequency, and second converter means for converting said first electrical signal into a second electrical signal having a second frequency greater than said first frequency; and
electrical conducting means disposed within one of said lumens and coupled to said second converter means for communicating said second electrical signal to said processing means.

12. An NMR probe as set forth in claim 11 wherein said probe comprises NMR visible material.

13. An NMR probe as set forth in claim 11 wherein said first converter means comprises a coil, said coil including metalization disposed on a surface of said integrated circuit.

14. An NMR probe as set forth in claim 11 wherein said probe further includes: means for cooling said integrated circuit to a substantially constant temperature below the temperature of the medium surrounding said probe.

15. An NMR probe as set forth in claim 14 wherein said means for cooling includes a plurality of Peltier junction devices integrated into said integrated circuit, and wherein said conducting means includes means for receiving an electrical driving signal for driving said Peltier junction devices, said conducting means also including means for conducting said driving signal to said Peltier junction devices.

16. An NMR probe as set forth in claim 15 wherein said Peltier junction devices are disposed proximate to said coil for reducing thermo-resistive emissions of said coil.

17. An NMR probe as set forth in claim 11 wherein said conducting means includes means for receiving an electrical perturbation signal at a selected perturbation frequency and for conducting said perturbation signal to said coil so that said coil can radiate an electromagnetic field in response to said perturbation signal for selectively modulating the magnetic polarization of a sample proximate to said integrated circuit.

18. An NMR probe for converting an NMR spectrum into an electrical signal analyzable by a processing means which includes a means for generating a control signal at a selected frequency, said probe comprising:
a probe body having a distal end;
a plurality of lumens disposed longitudinally within said probe body;
an integrated circuit carried at said distal end of said probe body, said integrated circuit including first converter means for converting detected NMR emissions into a first electrical signal having a first frequency, and second converter means for converting said first electrical signal into a second electrical signal having a second frequency greater than said first frequency; and
electrical conducting means disposed within one of said lumens and coupled to said second means for communicating said second electrical signal to said processing means;
said second converter means comprising:
a passive parametric amplifier having an integrated circuit capacitor, said capacitor having a capacitance which can be sinusoidally varied in response to said control signal, said second frequency being the sum of said first and said selected frequencies; and
means for coupling said control signal to said parametric amplifier.

19. An NMR probe as set forth in claim 18 further comprising means for generating and coupling a reverse biasing potential to said integrated circuit, wherein said capacitor includes:
an integrated circuit diode having a p-n junction coupled to said reverse bias coupling means, the depletion region width of said reverse biased p-n junction varying in response to said control signal.

20. An NMR probe as set forth in claim 19 wherein said conducting means includes one or more coaxial cables, each of said cables being disposed within an associated one of said lumens.

21. A system for in vivo sensing of RF energy emanating from an organism exposed to an NMR scanner comprising:
means for receiving RF energy emanating from within an organism in response to said NMR scanner, said receiving means being dimensioned for insertion into said organism, said receiving means comprising means for generating an electrical signal having a strength and frequency related to the strength and frequency, respectively of said RF energy, the frequency of said electrical signal being greater than the frequency of said RF energy
means for inserting said receiving means into an orifice in said organism and for localizing said receiving means at an area of interest within said organism, said receiving means being incorporated within said inserting means.

22. A system in accordance with claim 21 wherein said inserting means includes a tube adapted for inserting said receiving means into a cavity in said organism, said receiving means being disposed at a distal end of said tube.

23. A system as set forth in claim 21 wherein said inserting means includes a catheter adapted for inserting said receiving means into a blood vessel in said organism, said receiving means being disposed at a distal end of said catheter.

24. A system as set forth in claim 21 wherein said system further includes:
means for cooling said receiving means to a preselected temperature when said receiver is placed in said organism.

25. A system as set forth in claim 24 wherein said inserting means includes an endoscopic tube having fluid channels adapted for communicating cooling fluid from a source of cooling fluid to said receiving means, said receiving means being disposed at a distal end of said tube.

26. A system as set forth in claim 24 wherein said inserting means includes a catheter adapted to be inserted into a vessel of said organism and having fluid channels adapted for communicating cooling fluid from a source of cooling fluid to said receiving means, said receiving means being disposed at a distal end of said catheter.

27. A system in accordance with claim 21 wherein said receiving means comprises a coil.

28. A method for in vivo sensing of RF energy from an area of interest within an organism exposed to an NMR scanner comprising:
   providing an RF receiver dimensioned to be received within said organism for sensing the strength and frequency of said RF energy and for generating an electrical signal having a strength related to the strength of said RF energy and a frequency related to, and greater than, the frequency of said RF energy; and
   placing said RF receiver proximate to said area of interest.

29. A method as set forth in claim 28 wherein said placing step includes:
   attaching said receiver to a distal end of a tube; and
   inserting said tube into an orifice of said organism communicating with an organ of said organism to position said receiver proximate to said area of interest.

30. A method as set forth in claim 28 wherein said placing step includes:
   attaching said receiver to a distal end of a catheter; and
   inserting said catheter into a vessel of said organism to position said receiver proximate to said area of interest.

31. A method as set forth in claim 28 wherein said method further includes:
   cooling said receiver to maintain a selected temperature when said receiver is placed in said organism.

* * * * *

UNITED STATES PATENT AND TRADEMARK OFFICE
CERTIFICATE OF CORRECTION

PATENT NO. : 4,672,972

DATED : June 16, 1987

INVENTOR(S) : Howard R. Berke

It is certified that error appears in the above-identified patent and that said Letters Patent is hereby corrected as shown below: Title page:

In the Abstract, line 5, "receivied" should be --received--.

Column 3, line 47, after "that" insert --are--.

Column 3, line 51, "182" should be --18A--.

Column 3, line 59, after "processor" delete ",".

Column 5, line 5, after "components." insert --Integrated circuit 50 includes an integrated circuit coil 52 comprising multiple nested coils 52A-H; this integrated circuit can be fabricated as described above.--.

Column 8, line 6, after "second" insert --converter--.

Signed and Sealed this

Twenty-sixth Day of December, 1989

Attest:

JEFFREY M. SAMUELS

*Attesting Officer*   *Acting Commissioner of Patents and Trademarks*